(12) United States Patent  (10) Patent No.: US 8,831,739 B2
McCreery et al.  (45) Date of Patent: Sep. 9, 2014

(54) MICROELECTRODE ARRAY FOR CHRONIC DEEP-BRAIN MICROSTIMULATION FOR RECORDING

(75) Inventors: Douglas B. McCreery, Pasadena, CA (US); Martin Han, Pasadena, CA (US)

(73) Assignee: Huntington Medical Research Institutes, Pasadena, CA (US)

( * ) Notice: Subject to any disclaimer, the term of this patent is extended or adjusted under 35 U.S.C. 154(b) by 543 days.

(21) Appl. No.: 11/446,556

(22) Filed: Jun. 2, 2006

(65) Prior Publication Data

US 2006/0276866 A1  Dec. 7, 2006

Related U.S. Application Data

(60) Provisional application No. 60/687,197, filed on Jun. 2, 2005.

(51) Int. Cl.
*A61N 1/00* (2006.01)
*A61B 5/04* (2006.01)
*A61N 1/05* (2006.01)
*A61B 5/00* (2006.01)

(52) U.S. Cl.
CPC .............. *A61N 1/0534* (2013.01); *A61B 5/685* (2013.01); *A61N 1/05* (2013.01)
USPC .......................................... 607/116; 600/378

(58) Field of Classification Search
CPC ......... A61N 1/05; A61N 1/0534; A61B 5/685
USPC .................. 600/378; 607/116, 117, 118, 119, 607/122–123, 126, 128
See application file for complete search history.

(56) References Cited

U.S. PATENT DOCUMENTS

| 4,245,645 | A | * | 1/1981 | Arseneault et al. | 600/378 |
|---|---|---|---|---|---|
| 4,333,469 | A | * | 6/1982 | Jeffcoat et al. | 607/5 |
| 4,386,602 | A |  | 6/1983 | Sheldon et al. | |
| 4,401,126 | A | * | 8/1983 | Reenstierna | 607/125 |
| 4,461,304 | A | * | 7/1984 | Kuperstein | 600/378 |
| 4,721,551 | A | * | 1/1988 | Byers et al. | 623/24 |
| 5,466,253 | A | * | 11/1995 | Doan | 607/122 |
| 5,515,848 | A | * | 5/1996 | Corbett et al. | 600/377 |
| 5,999,859 | A | * | 12/1999 | Jolly | 607/137 |
| 6,038,478 | A | * | 3/2000 | Yuen et al. | 607/74 |
| 6,094,598 | A |  | 7/2000 | Elsberry et al. | |

(Continued)

OTHER PUBLICATIONS

Kuperstein, Michael and Whittington, Douglas A. "A Practical 24 Channel Microelectrode for Neural Recording in Vivo" IEEE Transactions of Biomedical Engineering, vol. BME-28, No. 3, Mar. 1981.*

(Continued)

*Primary Examiner* — Niketa Patel
*Assistant Examiner* — William Levicky
(74) *Attorney, Agent, or Firm* — Christie, Parker & Hale, LLP

(57) ABSTRACT

The invention relates to a multielectrode probe having a silicon substrate which supports multiple conductive electrodes for deep-brain electrical stimulation or recording of neural responses. The substrate has an upper end with multiple conductive portions for bonding to lead wires, and an elongated shank extends from the upper end. The shank supports multiple spaced-apart electrodes, typically ten in number, and conductive traces electrically connect the electrodes and conductive traces. Multiple probes are combined, and supported as an array by a cylindrical alignment cylinder.

16 Claims, 4 Drawing Sheets

(56) References Cited

U.S. PATENT DOCUMENTS

| | | | |
|---|---|---|---|
| 6,190,350 | B1 | 2/2001 | Davis et al. |
| 6,330,466 | B1* | 12/2001 | Hofmann et al. ............. 600/378 |
| 6,366,813 | B1* | 4/2002 | DiLorenzo ...................... 607/45 |
| 6,855,143 | B2* | 2/2005 | Davison et al. ................. 606/41 |
| 7,006,859 | B1* | 2/2006 | Osorio et al. ................. 600/378 |
| 7,181,288 | B1* | 2/2007 | Rezai et al. ................... 607/116 |
| 2002/0188310 | A1* | 12/2002 | Seward et al. ................ 606/185 |
| 2002/0198582 | A1* | 12/2002 | Edell et al. .................... 607/116 |
| 2003/0100823 | A1* | 5/2003 | Kipke et al. .................. 600/378 |
| 2004/0064158 | A1* | 4/2004 | Klein et al. ....................... 607/9 |
| 2004/0199235 | A1* | 10/2004 | Younis ........................... 607/116 |
| 2004/0243205 | A1* | 12/2004 | Keravel et al. ................ 607/116 |
| 2005/0021103 | A1* | 1/2005 | DiLorenzo ...................... 607/45 |
| 2005/0107742 | A1* | 5/2005 | Ghovanloo et al. ........... 604/117 |
| 2005/0143790 | A1* | 6/2005 | Kipke et al. .................... 607/60 |
| 2010/0331935 | A1* | 12/2010 | Tabada et al. ................. 607/116 |

OTHER PUBLICATIONS

McCreery, Douglas et al.; "A Microelectrode Array for Deep-Brain Stimulating and Recording"; Abstract of poster Presented at 2002 deep brain symposium, Washington D.C.; Neural Engineering Laboratory; Huntington Medical Research Institutes, Pasadena, California; Supported by grant NS40860-02 from the National Institutes of Health;1 page.

McCreery, Douglas et al.; "A Microelectrode Array for Deep Brain Stimulating and Recording"; Neural Engineering Program Huntington Medical Research Institutes; 2003 DBS Consortium Meeting; Wyndham Washington Hotel, Washington, D.C.; Sep. 29-30, 2003; Supported by grant NS40860-02 from the National Institutes of Health; 14 pages.

McCreery, Douglas B.; Grant Application and Research Plan; "Microelectrode Arrays for Deep Brain Stimulation and Recording"; Grant No. 5R01NS040860-03; RFA NS-99-006; Feb. 10, 2000; face page and pp. 30-58.

McCreery, Douglas B.; Abstract; "Microelectrode Arrays for Deep Brain Stimulation and Recording"; Grant No. 5R01NS040860-03; RFA NA-99-006; 1 page.

McCreery, Douglas et al.; "A Microelectrode Array for Deep-Brain Stimulating and Recording"; Neural Engineering laboratory, Huntington Medical Research Institutes; 2002 DBS Consortium Meeting; Wyndham Washington Hotel, Washington, D.C.; Supported by grant NS40860-02 from the National Institutes of Health; 14 pages.

McCreery, Douglas et al.; "A Microelectrode Array for Deep-Brain Stimulating and Recording"; Abstract of poster Presented at 2003 deep brain symposium, 2003; Washington D.C.; Neural Engineering Laboratory; Huntington Medical Research Institutes, Pasadena, California; Supported by grant NS40860-02 from the National Institutes of Health; 1 page.

* cited by examiner

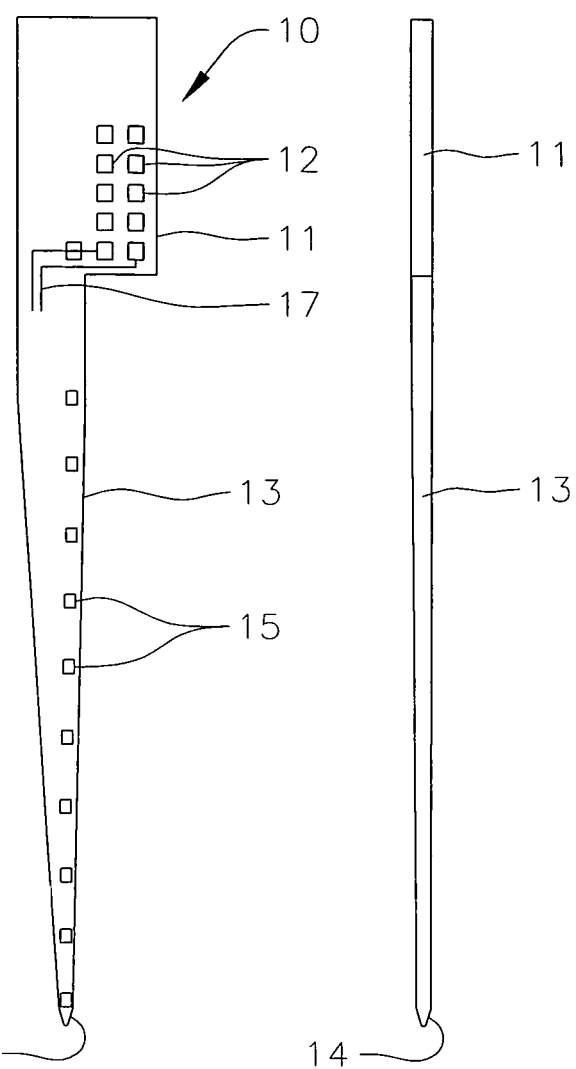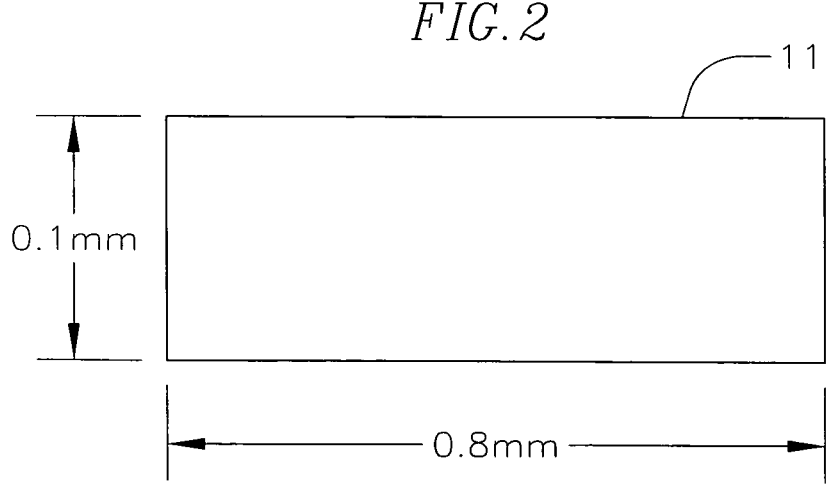

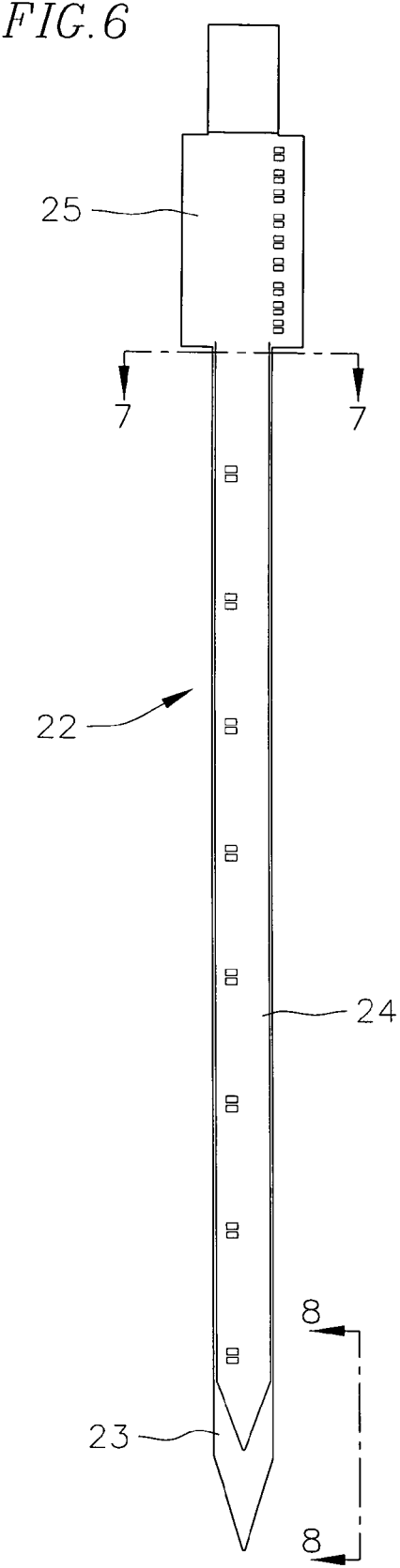
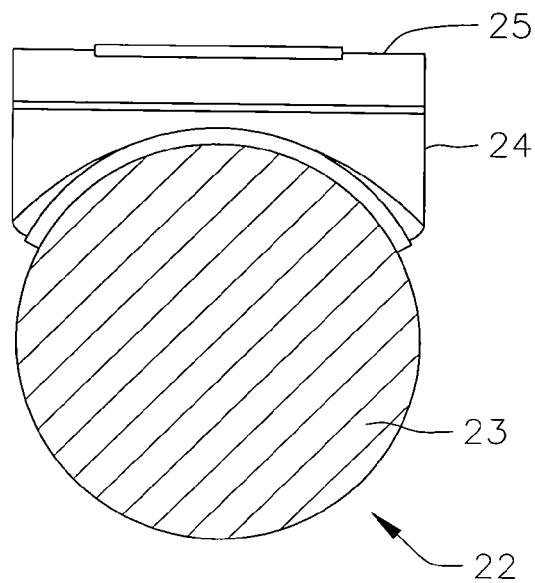
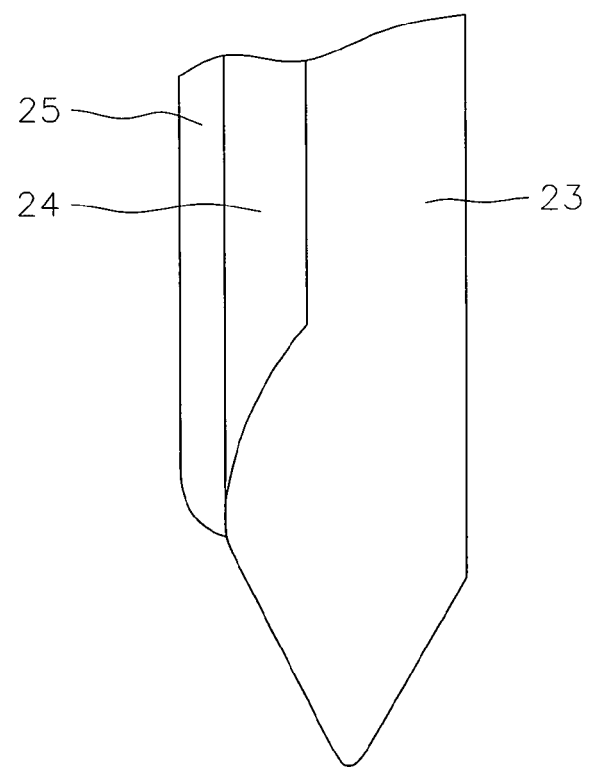

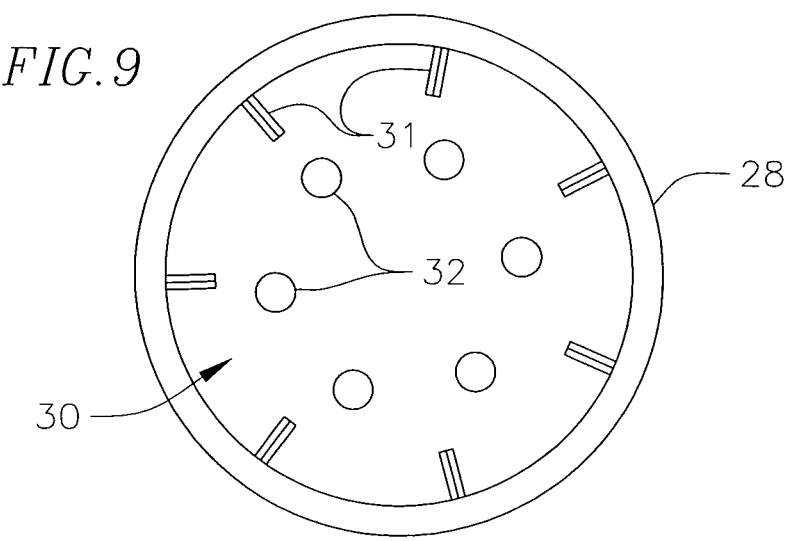
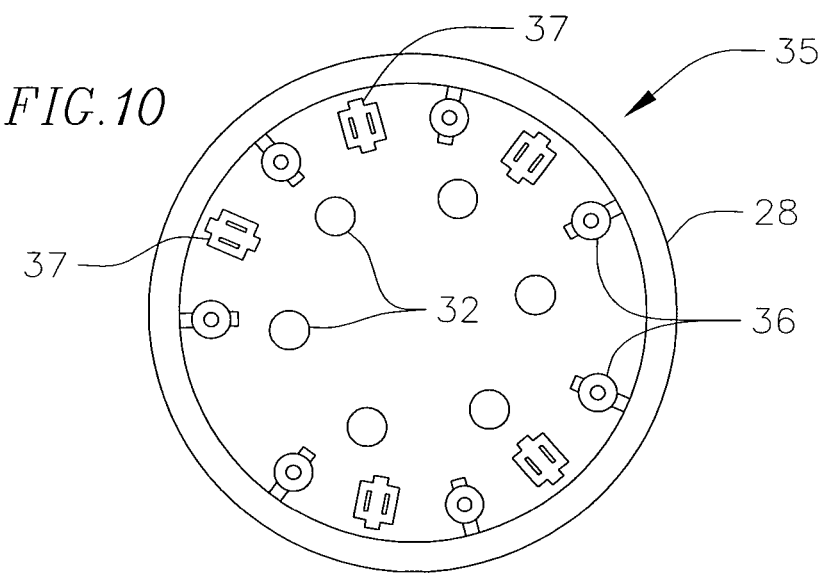
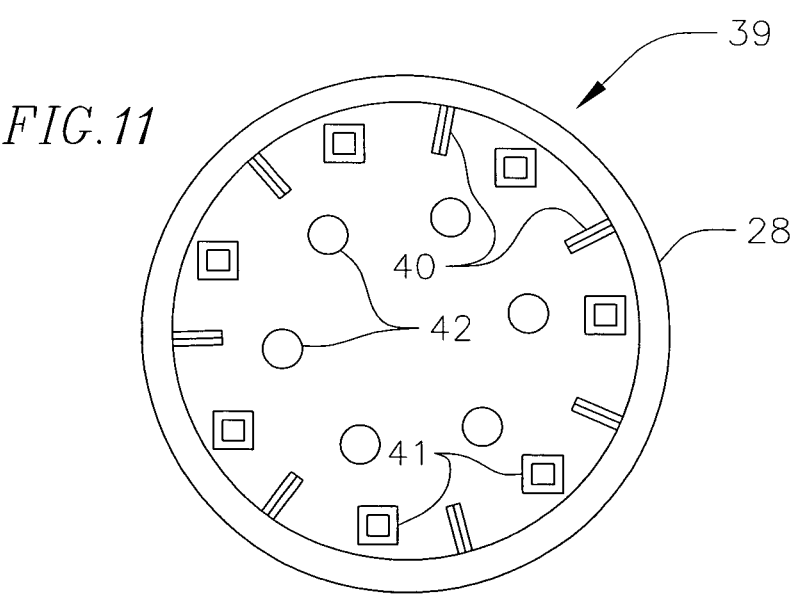

MICROELECTRODE ARRAY FOR CHRONIC DEEP-BRAIN MICROSTIMULATION FOR RECORDING

CROSS REFERENCE TO RELATED APPLICATION

This application is in part based on, and claims the filing date of U.S. Provisional Application 60/687,197 filed Jun. 2, 2005.

BACKGROUND OF THE INVENTION

This invention relates to a microelectrode array for implantation in deep-brain nuclei such as the subthalamic nucleus and the internal segment of the globus pallidus.

Electrical stimulation in deep brain structures (deep brain stimulation, or "DBS") has developed into an effective treatment modality for advanced Parkinson's Disease and essential tremor. DBS also is being evaluated as a treatment for other neurological conditions and appears to be useful in the treatment of several types of dystonias and hyperkinetic disorders. While the range of clinical applications for DBS has expanded in recent years, its mechanism of action is not completely understood. Studies directed towards an elucidation of the physiologic underpinnings of DBS certainly have been aided by a previously developed microelectrode array for chronic implantation into animals, including subhuman primates, and which delivers highly localized electrical stimulation into the target nucleus, and which includes the capability of monitoring the response to the electrical stimulation by individual neurons in the target nucleus. It is important that the microelectrodes be able to deliver stimulation for an extended interval, and without injury to the tissue. An array of independently controllable stimulating microelectrodes distributed throughout the target nucleus would permit precise control of the spatial distribution of the stimulation, by stimulating either with single microelectrodes or with a subgroup of microelectrodes that could be pulsed either simultaneously or sequentially. This capability is absent in the arrays now in clinical use.

By improving the effectiveness and acceptability of DBS therapy, this technology will improve the quality of life for persons with Parkinson's Disease and other movement disorders. In addition to its applicability in a clinical device, this technology will be valuable in animal models used to investigate the mechanisms by which deep brain stimulation can ameliorate the symptoms of Parkinson's Disease and other movement disorders, and thereby will contribute further to the effective treatment of these disorders.

The previously developed array of microelectrodes, suitable for long-term implantation into the human subthalamic nucleus (STN) or other deep brain nuclei, including the internal segment of the globus pallidus (GPi), is able to record from single neurons in many parts of the target nucleus, can deliver localized microstimulation and localized "sculpted" stimulation at many separate locations within the target nucleus, but also is fully "backward compatible" (can deliver the same maximum stimulus at the same number of sites) as the arrays now in clinical service. Such an array could form the nucleus of a next generation of deep-brain stimulator that would include an adaptive controller that uses the neuronal recordings to adjust the stimulation.

The previously developed array uses 16 discrete activated-iridium microelectrodes. This device can deliver highly localized electrical stimulation within the target, and also can record the action potentials from single neurons, while inducing minimal disruption of the tissues of the target nucleus. The present invention uses new technology to overcome a significant limitation of the previously developed array, namely, its limited number of independent stimulating and recording sites.

The invention is an impovement and extension of the previously developed array of 16 discrete activated-iridium microelectrodes (the Discrete Iridium Array for Deep Brain Microstimulation and Recording, "DIADMAR"). This device can deliver highly localized electrical stimulation within the target, and also can record the action potentials from single neurons, while inducing minimal disruption of the tissues of the target nucleus. The invention uses state-of-the-art technology to overcome a significant limitation of this device for clinical use; namely its limited number of independent stimulating and recording sites. The primary technology used to fabricate the silicon probe (Bosch-process deep reactive ion etching), is known, and has only recently been applied to the fabrication of silicon microprobes. The novel feature of the invention is the manner in which multiple silicon probes will be incorporated into a device that will allow selective and targeted stimulation throughout the recording nucleus, concomitant recording of neuronal activity throughout the nucleus, and full compatibility with the current clinical devices, in a configuration that will induce a minimum of disruption and tissue injury within the target nucleus.

The invention uses an array of multisite silicon-substrate probes which will span the motor portion of the human STN and Gpi. The silicon probes will have mechanical properties suitable for inclusion in an array for clinical use. The number of electrodes sites required to span and populate the human STN or Gpi is too large to be realized using discrete microelectrodes, necessitating the use of multisite silicon probes. The invention uses state-of-the-art micromachining and photolithographic techniques to place a large number of stimulating and recording sites within the target nucleus, while minimizing the amount of tissue displaced and thus minimizing the risk of tissue injury. The array incorporates up to 70 microstimulating and 70 recording electrode sites, for implantation into the human STN or Gpi. Each array will preferably include 6 discrete iridium "minielectrodes" that can safely inject up to 400 nC/phase at 150 Hz. This will ensure that the device is backward compatible with the arrays now in clinical use for DBS. The recording microelectrodes will form the afferent limb of a "smart" (adaptive) stimulator that could automatically fine-tune the stimulus parameters in patients with Parkinson's Disease.

SUMMARY OF THE INVENTION

The invention relates to a multielectrode probe having a silicon substrate which supports multiple conductive electrodes for deep-brain electrical stimulation or recording of neural responses. The substrate has an upper end with multiple conductive portions for bonding to lead wires, and an elongated shank extends from the upper end. The shank supports multiple spaced-apart electrodes, typically ten in number, and conductive traces electrically connect the electrodes and conductive traces. Multiple probes are combined, and supported as an array by a cylindrical alignment cylinder.

BRIEF DESCRIPTION OF THE DRAWINGS

FIG. 1 is a front view of a multielectrode silicon-substrate probe according to the invention;

FIG. 2 is an enlarged top view of FIG. 1;

FIG. 3 is a side view on line 3-3 of FIG. 1;

FIG. 6 is a side view of a second embodiment of a multielectrode probe;

FIG. 7 is a top view on lie 7-7 of FIG. 6;

FIG. 8 is a side view on line 8-8 of FIG. 7;

FIG. 9 is a schematic end view of an array of multiple multielectrode probes contained within a circular shank;

FIG. 10 is similar to FIG. 9, but illustrating a different combination of probe types; and FIG. 11 is also similar to FIG. 9, but again showing a further different combination of probe types.

DESCRIPTION OF THE PREFERRED EMBODIMENTS

FIGS. 1-3 illustrate a multielectrode silicon-substrate probe 10 according to the invention. The silicon substrate is preferably formed by deep reactive-ion etching which can yield a relatively strong and rigid structure of up to at least 0.1 mm in thickness. The body of probe 10 has an enlarged upper end 11 with a width of about 0.8 mm, a height of about 2 mm, and a thickness of about 0.1 mm. The upper end is a bonding pad with multiple (presently ten) conductive portions 12, preferably gold, to which conducting lead wires (not shown) are attached. After the leads are attached, the upper end is coated with a silicone-elastomer.

Figure 4:
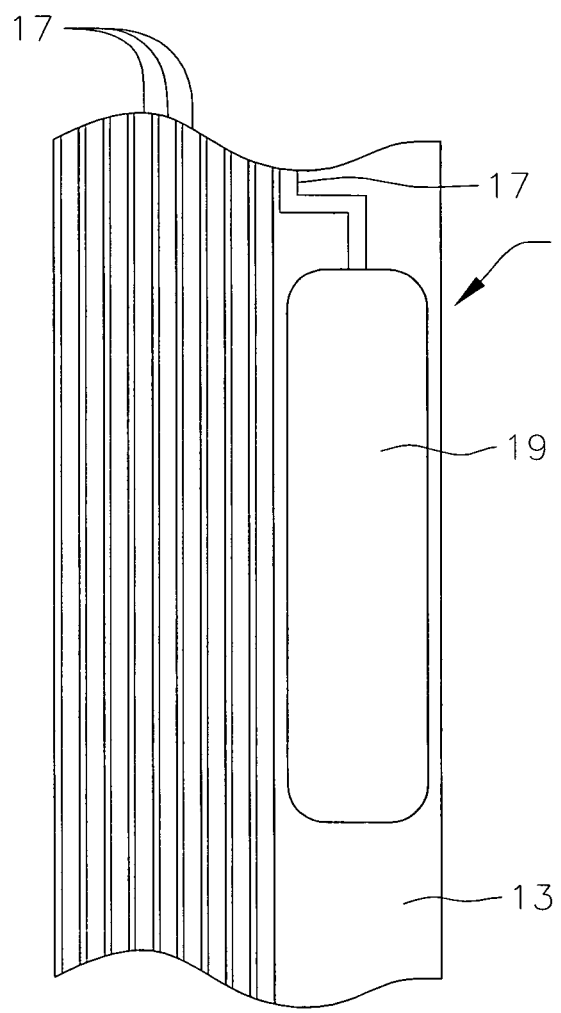
FIG. 4 is an enlarged partial of a shank of the probe, and showing a stimulating electrode and multiple connecting leads.
Figure 5:
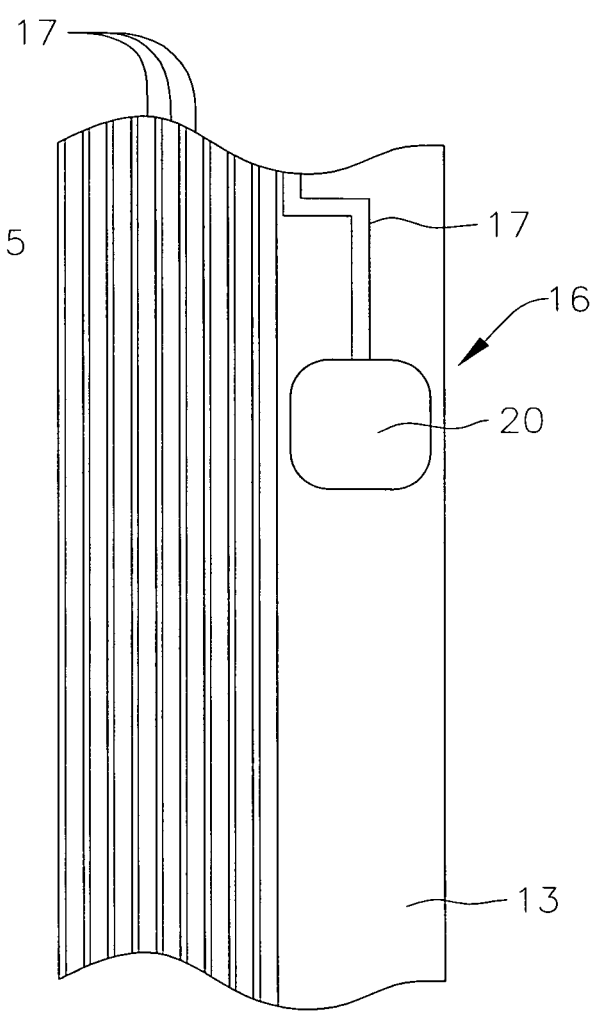
FIG. 5 is similar to FIG. 4, but showing a recording electrode.

Extending downwardly from the probe upper end is an elongated shank 13, about 10 mm in length. The shank has an upper-end width of about 0.4 mm, and tapers to a rounded tip 14. Commencing about 3 mm below upper end 11, there are ten stimulating-or-recording electrode sites 15 or 16 which are vertically spaced apart about 0.8 mm. These sites span target nuclei in the human brain, such as in the subthalmic nucleus. Ten conductive tracers 17 (preferably gold of about 0.2-mm thickness, deposited on titanium and platinum) extend between and electrically connect conductive portions 12 and stimulating electrodes 16 or recording electrodes 17 on the shank (FIGS. 4 and 5). Traces 17 are about 4 μm in width, and are spaced apart about 2 μm.

A stimulating-electrode site 15 is shown in greater detail in FIG. 4. Each site 15 has an activated-iridium stimulating electrode 19 of somewhat rectangular shape, and with rounded corners to minimize charge-density inhomogeneity. Electrode 19 is about 35 μm wide, and 290 μm high, providing a surface area to operate at charge densities as high as about 400 μC/cm². Activated-iridium electrode 19 is electroplated on an underlying gold surface on shank 13. One of the conductive traces 17 is bonded to electrode 19 as shown.

A recording-electrode site 16 is shown in FIG. 5, and is similar to the stimulating-electrode site, with the exception that a recording electrode 20 is smaller than electrode 19. The recording electrode is about 35 μm wide, and 30 μm high, again with rounded corners, and one of the conductive traces is bonded to electrode 20.

Each probe 10 is either a stimulating probe with ten electrodes 19, or a recording probe with ten electrodes 20. Preferably, a stimulating probe and a recording probe are secured together back-to-back, to form a composite probe which maximizes the number of electrode sites relative to the amount of tissue displaced by probe placement.

An alternative reinforced probe 22 is shown in FIGS. 6-8, and is useful should greater resistance to bending be needed during tissue insertion. Probe 22 is strengthened by a stiff iridium shaft 23 of about 75 μm diameter. A silicon probe 24 with a part-circle rear surface is secured to shaft 23 with a silicone-elastomer adhesive. A front surface 25 of probe 24 supports either ten stimulating electrodes or ten recording electrodes as described above. An upper end of probe 24 is a bonding pad 25 for conductive lead wires (not shown) as also described above.

FIGS. 9-11 illustrate various arrays of the above-described probes, the upper ends of which are arranged and supported within an alignment cylinder 28 (shown in end view) of about 6 mm length, and with an internal diameter of about 1.8 mm, and an outside diameter of about 2.0 mm. The alignment cylinder is preferably made of Type 316L stainless steel.

A first array 30 (FIG. 9) supports an outer ring of seven circumferentially arranged composite probes 31, each having ten recording electrodes, and ten stimulating electrodes. An inner ring of array 30 is formed by six discrete activated-iridium wire stimulating electrodes 32, each of about 75 μm diameter, ranging in length from 3 to 10 mm, and with exposed tip areas to inject up to 400 nC/phase, while not exceeding a charge density of 400 μC/cm². The body of electrode 32 is insulated with a material such as Parylene-C, but the insulation is ablated from a rounded tip of the electrode.

Use of electrodes 32 provides "backward compatibility" with deep-brain external equipment now in use. Array 30 has good functionality by affording great coverage of the target area with 70 stimulating and 70 recording sites, with a small number of probes for small volume and tissue displacement.

A second array 35 (FIG. 10) has an outer ring formed by seven reinforced stimulating probes 36, and seven reinforced recording probes 37, of the type described above for probe 22. An inner ring of discrete stimulating electrodes 32 again provides backward compatibility. A third array (FIG. 11) is similarly arranged, but with an outer ring of seven two-sided composite probes, and seven alternating discrete iridium neural-recording electrodes. Other array arrangements are possible.

What is claimed is:

1. A multielectrode probe for electrical stimulation of deep-brain nuclei for correction of movement disorders, or recording of neural responses, comprising:
    an enlarged upper end comprising a silicon-substrate body and a plurality of conductive portions for bonding to lead wires,
    an elongated, slender silicon-substrate shank extending from the enlarged upper end,
    a plurality of spaced-apart electrodes on the shank,
    a plurality of conductive traces, each conductive trace electrically connecting one of the plurality of conductive portions to one of the plurality of electrodes and extending from the enlarged upper end along the shank, and
    a slender elongated strengthening shaft adhered to the elongated, slender silicon-substrate shank along a length of the slender silicon-substrate shank.

2. The probe of claim 1, in which about ten electrodes are spaced along the shank for deep-brain electrical stimulation.

3. The probe of claim 1, in which about ten electrodes are spaced along the shank for recording neural response to electrical stimulation.

4. The probe of claim 1, in which the shank is about 10 mm in length.

5. The probe of claim 3 or 4, in which the conductive traces extend in parallel along the shank, the traces being about 4 μm in width, and being spaced apart about 2 μm.

6. The probe of claim 1, in which the electrodes are for electrical stimulation and made of activated iridium, each electrode being about 290 μm high, and 35 μm wide.

7. The probe of claim 1, in which the electrodes are for sensing of electrical neural responses to stimulation and made of activated iridium, each electrode being about 30 μm high, and 35 μm wide.

8. The probe of claim 1, wherein the slender elongated strengthening shaft comprises iridium.

9. The probe of claim 1, wherein a silicone-elastomer adhesive adheres the shank to the shaft.

10. The probe of claim 1, wherein the shaft is cylindrical.

11. The probe of claim 1, wherein the shank defines a longitudinal part-circular trough to which the shaft is adhered.

12. An array of multielectrode probes for deep-brain implantation, the array comprising:
 a cylindrical alignment cylinder; and
 an array of parallel multielectrode probes having ends supported within the cylindrical alignment cylinder, each of the probes having multiple electrodes for electrical stimulation of deep-brain nuclei, and recording of neural responses, each of the probes comprising an elongated, slender silicon-substrate shank having an enlarged upper end with multiple conductive portions thereon for bonding to lead wires and an elongated iridium shaft adhered to the elongated, slender silicon-substrate shank along a length of the slender silicon-substrate shank.

13. The array of claim 12, and further comprising a plurality of discrete activated-iridium wire stimulating electrodes.

14. A multielectrode probe for electrical stimulation of deep-brain nuclei for correction of movement disorders, or recording of neural responses, comprising:
 an enlarged upper end comprising a silicon-substrate body and a plurality of conductive portions for bonding to lead wires,
 an elongated, slender silicon-substrate shank extending from the enlarged upper end, the shank defining a longitudinal part-circular trough,
 a plurality of spaced-apart electrodes on the shank,
 a plurality of conductive traces, each conductive trace electrically connecting a respective conductive portion to a respective electrode and extending from the enlarged upper end along the shank, and
 an elongated iridium strengthening shaft adhered to the longitudinal trough of the elongated, slender silicon-substrate shank, the shaft being adhered to the shank using a silicone-elastomer adhesive.

15. The probe of claim 14, wherein the shaft is cylindrical.

16. The probe of claim 14, wherein the electrodes are located on a side of the shank opposite the longitudinal trough.

* * * * *